United States Patent [19]

Fraley et al.

[11] Patent Number: 5,667,795
[45] Date of Patent: Sep. 16, 1997

[54] PESTICIDAL MICRONUTRIENT COMPOSITIONS CONTAINING ZINC OXIDE

[75] Inventors: Richard Wayne Fraley, Kingwood, Tex.; Paul Rogers, Greenwood, Ind.

[73] Assignee: ISK Biosciences Corporation, Mentor, Ohio

[21] Appl. No.: 680,434

[22] Filed: Jul. 15, 1996

Related U.S. Application Data

[63] Continuation of Ser. No. 192,852, Feb. 7, 1994.

[51] Int. Cl.$^6$ .................................................. A01N 25/14
[52] U.S. Cl. .................... 424/405; 424/409; 424/641; 504/101; 504/141; 504/187; 514/494; 514/741
[58] Field of Search .......................... 424/405, 421, 424/409; 504/101, 141, 187; 514/494, 741; 71/64.08, 64.13

[56] References Cited

U.S. PATENT DOCUMENTS

| | | |
|---|---|---|
| 3,620,708 | 11/1971 | Ott .................................... 71/33 |
| 3,662,064 | 5/1972 | Wijmenga et al. ............... 424/145 |
| 3,954,992 | 5/1976 | Davidson ........................ 424/287 |
| 4,356,021 | 10/1982 | Kenton ............................. 71/30 |
| 4,556,426 | 12/1985 | Chesney, Jr. et al. .......... 106/18.32 |
| 4,861,380 | 8/1989 | Campbell et al. ............... 106/504 |
| 4,980,367 | 12/1990 | Cuo et al. ....................... 514/383 |
| 5,129,950 | 7/1992 | Hyczg et al. .................... 71/118 |

FOREIGN PATENT DOCUMENTS

| | | |
|---|---|---|
| 1521463 | 3/1968 | France . |
| 2615069 | 5/1987 | France . |
| 57-099506 | 6/1982 | Japan . |
| 8201980 | 6/1982 | WIPO . |

OTHER PUBLICATIONS

Fertilizers and Fertilization, Introduction and Practical Guide to Crop Fertilization, by Arnold Finck, 1982.

*Primary Examiner*—Neil S. Levy
*Attorney, Agent, or Firm*—Thompson Hine & Flory LLP

[57] ABSTRACT

Chlorothalonil compositions which are useful in formulating aqueous pesticidal sprays in which zinc oxide is present as a micronutrient; the compositions are particularly useful for application to potatoes.

19 Claims, No Drawings

PESTICIDAL MICRONUTRIENT COMPOSITIONS CONTAINING ZINC OXIDE

This is a continuation of application Ser. No. 08/192,852 filed Feb. 7, 1994, pending.

BACKGROUND

This invention relates to a pesticidal formulation containing zinc oxide and, in particular, a pesticidal formulation containing zinc oxide for use on potatoes, dry beans, and other crops. Zinc provides an essential element for plant nutrition and zinc deficiency commonly causes poor plant growth. The modes currently used to apply zinc to plants to prevent or remedy zinc deficiency are clear liquids and suspensions of a soluble zinc compound such as zinc sulfate and various zinc chelates. Zinc oxide, although cheaper than zinc sulfate, has not been generally used because of its recognized inability to efficiently enter the plant.

U.S. Pat. No. 3,130,034 to Young describes one method of overcoming zinc deficiencies. Young teaches an aqueous solution formulated by incorporating zinc sulfate in aqueous ammonia to provide a solution with a desirable salt out temperature. Unfortunately, aqueous solutions of zinc sulfates corrode milled steel and form large quantities of scale and rust in process tanks and equipment.

U.S. Pat. No. 3,620,708 to Ott teaches another method for delivery of zinc to plants. The Ott formulation consists of water, zinc oxide, phosphorous pentoxide, and ammonia to create an ammonia based solution fertilizer providing nitrogen, phosphorous and solubilized zinc.

The methods that have been used in the art to deliver zinc to plants use zinc in the form of zinc salts and chelates. Because of the high solubility of zinc salts in water, a zinc salt, such as zinc sulfate or a chelated form, delivers zinc through the roots or foliage systems of a plant. These are the preferred and accepted methods for increasing the zinc levels within a plant. One disadvantage with these forms of zinc is that they are very soluble in water and tend to wash off foliage with dew and precipitation. Furthermore, zinc salts are more difficult and expensive to formulate in combination with conventional pest control agents.

A need has developed for a method which more effectively delivers zinc to plants. A further need has developed for a delivery system which is less expensive than current systems to formulate and which will be less likely to wash off the plants in heavy precipitation.

SUMMARY OF INVENTION

A pesticidal composition has been developed which provides a method for delivering elemental zinc, in the form of chemically unmodified zinc oxide, an essential nutrient to promote the growth of potato, dry bean and other plants. The composition of this invention includes both zinc oxide and a pesticide. Zinc oxide provides an inexpensive method to deliver elemental zinc to plants and legumes which require large concentrations of elemental zinc to thrive in their environments. Zinc oxide processed into this formulation makes it highly tenacious due to the low water solubility of zinc oxide, the formulation ingredients and its very fine particle size. Thus, it is slow to wash off leaves and from the soil during prolonged periods of precipitation. The zinc oxide can be processed into this composition by any of several conventional milling processes such as wet milling and/or air milling.

This invention provides three compositions for delivering zinc oxide in combination with a pesticide to plants and, more particularly, to potatoes. The first is an aqueous homogeneous suspension; the second is a wettable powder formulation; and the third method is a spray dried dispersible granule. All of these systems provide a novel manner of delivering higher concentrations of elemental zinc to plants at low cost and in a very stable form.

This invention also provides several pesticides, defined below, which are deliverable to the plants along with the zinc. These pesticides provide a biocidal element to the formulations for delivering zinc.

DETAILED DESCRIPTION

This invention provides three pesticidal compositions useful in delivering zinc in the form of zinc oxide to plants. The first is an aqueous concentrate, which is the preferred method for delivering zinc. The second composition is a wettable powder. The third composition is a spray dried dispersible granule. The latter two compositions include many of the same ingredients which are included in the first. For that reason, the common elements will be discussed in the description of the first composition and will be referenced back to the original description in the subsequent description of the other two compositions.

Aqueous Concentrates:

The aqueous concentrate of this invention comprises an aqueous homogeneous suspension of zinc oxide and at least one solid or emulsified liquid pesticidal ingredient, with water solely being employed as the liquid suspending medium. The nature of the components and the quantities, by weight, of each which constitute a preferred embodiment of the composition of this invention are the following:

10–60% of at least one finely-dispersed essentially water insoluble pesticide;
1–10% of zinc oxide;
1–10% of a nonionic surfactant;
0–4.0% of an anionic surfactant;
0.02–1.0% of a heteropolysaccharide gum;
0–5.0% of an antifoaming agent;
0–10% of an anticaking agent;
0–2.0% of a protective colloid;
0–10% of a freeze point depressant;
0–1.0% of a preservative; and
0–5.0% of a chelating agent, with water being in sufficient quantity to provide, in combination with other ingredients, 100 parts of a finished composition.

As used herein in the specification and claims, the terms "active," "pesticidally-active," "pesticide," "pesticidal," and the like, are each intended to refer to toxicants and to biological compositions containing these chemicals which are effective in killing, preventing, or controlling the growth of undesirable pests, i.e., plants, insects, mice, microorganism, algae, fungi, bacteria, and the like, these chemicals and compositions being commonly known as, e.g., insecticides, miticides, bactericides, algacides, fungicides, nematocides, herbicides, etc. The toxicant chemicals employed in the pesticide formulations of this invention are essentially insoluble in water, that is to say, they are typically less than 1% soluble in water. Exemplary of specific toxicant compounds known and used as pesticides which suitably may be employed in the composition of this invention include Captan, Chlorothalonil, copper hydroxide, copper oxychlorides, copper resinates, Cypraconzaole, Fluazinam, Flutolanil, Hexaconazole, Iprodione, Maneb, Metalaxyl, Propiconazole, Tebuconazole and Triadimefon, with Chlorothalonil being preferred.

In general, the pesticide content of the concentrates of this invention may vary from about 10 to 60%, by weight. In those compositions containing high solids content, the pesticide content typically varies from 40 to 60%, by weight.

The pesticide and zinc oxide are employed in a finely-divided form having an average particle size ranging preferably between about 1 to 10 microns. It is desirable that the pesticide materials and zinc oxide have an average particle size within the stated range so that the greatest surface area per unit weight of formulation will be provided, thereby allowing the pesticide and zinc oxide to be most homogeneously suspended. Likewise, pesticides which are extremely finely-divided provide greater biological activity per unit area of plant tissue. Also, the maximized surface area of zinc oxide maximizes its rate of dissolution in water and thereby its translocation into the plant tissue. In preparing the pesticidal compositions of this invention, in order to assure that the pesticide ingredient will have the desired average particle size, it may sometimes be necessary to subject the pesticide to airmilling, hammer milling, ball milling, or other conventional comminuting treatments known in the art.

In usual practice herein, concentrates of the invention will contain either one or a combination of solid, and sometimes liquid, essentially water-insoluble pesticide components. One should note, however, that it is also possible to prepare suitable compositions which incorporate, in addition to at least one of the previously described pesticides, one or more solid, water-soluble pesticide components. In these compositions, the soluble pesticide will of course be in solution in water as the continuous phase.

The micronutrient used in this invention is zinc oxide. The zinc oxide is present in the aqueous concentrate in a total weight percent of 1.0 to 10.0%, and in the preferred embodiment, 4.0 to 7.0%. Studies demonstrating the efficacy of zinc oxide as a micronutrient have demonstrated that zinc levels in the foliage of potato and dry bean are increased to recognized optimum content by applications of specially formulated pesticide plus zinc oxide. Zinc levels in dry bean were increased from 30 ppm to 80 ppm and from 20 ppm to 80 ppm in potato, thus, meeting the performance of higher cost zinc nutrients.

The heteropolysaccharide gum and the nonionic/anionic surfactants, in combination, comprise the dispersing-suspending system of the flowable composition of this invention. It is critical to employ these components in certain prescribed ratios both in relation to each other and to the concentration of pesticide component in order to obtain compositions with the desire storage stability and water-dispersibility.

The terms "heteropolysaccharide" and "heteropolysaccharide gum" as used herein are meant to include the use of the polysaccharide in the form of the colloid and its salts, e.g., amine derivatives prepared by the method disclosed, for example, in U.S. Pat. No. 3,244,695.

The heteropolysaccharide, which is commonly designated in the art as a xanthan gum, is a high molecular weight linear exocellular material prepared by the action of bacteria of the genus Xanthomonas on carbohydrates. It has a molecular weight in excess of 200,000 preferably over 1 million. A variety of carbohydrates can be fermented with various species of the genus Xanthomonas to produce the heteropolysaccharide. Examples of suitable bacterium species of the genus Xanthomonas include *X. campestris, X. carotate, X. inconue, X. begoniae, X. malvacerum, X. vesicatoria, X. translucens*, and *X. vasculorum*, among others. Suitable carbohydrates include, e.g., glucose, sucrose, fructose, maltose, lactose, galactose, soluble starch, corn starch, potato starch, and the like. Preparation of heteropolysaccharides suitably used herein is described in greater detail but not solely in U.S. Pat. No. 3,020,206.

In general, any nonionic surfactant which has a suitable hydrophilic-lyophilic balance may be employed in the suspending-dispersing system of the flowable composition of this invention. Specific suitable surfactants are selected from the following classes or types of nonionic surfactant materials: ethoxylated alkylphenols (also designated in the art as alkylaryl polyether alcohols); ethoxylated aliphatic alcohols (or alkyl polyether alcohols); ethoxylated fatty acids (or polyoxyethylene fatty acid esters); ethoxylated anhydrosorbitol esters (or polyoxyethylenesorbitan fatty acid esters); tristyrlphenols; and ethoxylated polyoxypropylene glycols (polyalkylene oxide block copolymers). Of these, the preferred surfactants at present are ethoxylated polyoxypropylene glycols i.e. polyalkylene oxide block copolymers and the ethoxylated alkylphenols, i.e. alkylaryl polyether alcohols of the general formula:

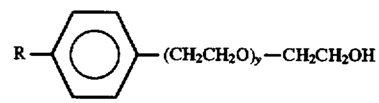

wherein R=a $C_8$–$C_{12}$ linear or branch-chained alkyl group and y=an integer of 8–30, as formulations with both optimum water dispersibility and adequate storage stability are obtained by using these surfactants. Within this class, especially preferred are those alkylaryl polyether alcohols wherein R is a $C_9$ or $C_{10}$ alkyl group and y is an integer of 9–15. Of the ethoxylated polyoxypropylene glycols, ethylene oxide-propylene oxide block copolymer, available from B.A.S.F., is preferred.

In practice of the invention, any of the previously described nonionic surfactant compounds generally may be employed as the sole surfactant in the composition, or two or more of these compounds may be employed in combination. Likewise, a portion of any of these compounds designated herein as primary surfactants, suitably may be replaced by an equivalent quantity of a nonionic surfactant such as, e.g., a liquid lower alkylene glycol ester of a fatty acid, as a secondary surfactant. Also, anionic surfactants such as sodium salts of naphthalene sulfonate formaldehyde condensates and cationic salts of lignosulfonates in concentrates of 0.1 to 4.0 percent may be used to improve resuspensibility and spontaneity of the suspension concentrate.

The heteropolysaccharide, i.e., xanthan gum, is employed in the composition generally in an amount ranging between 0.02 and 1.0 parts per 100 parts of total formulation while from 1.0 to 10 parts of the nonionic surfactant moiety generally is incorporated per 100 parts of the formulation. In compositions of high pesticide solids content, the xanthan gum generally is employed in an amount ranging from 0.05 to 0.75 parts and the surfactant in an amount ranging generally from 1 to 7 parts per 100 parts of formulation. If each of these components is employed separately as the sole suspending or dispersing agent in otherwise similar formulations, the solid pesticide components soon settle out of the continuous water phase. During the prolonged length of time such compositions are then allowed to stand after solids settling, it often becomes extremely difficult to resuspend the solids therein, even with vigorous and prolonged agitation.

In the pesticide composition of this invention, it is generally required to employ both the heteropolysaccharide and surfactant components within the ranges stated above in order to obtain the desired composition. Formulations containing amounts of these components outside these ranges will tend to be too thin or too thick and nonflowable, exhibiting inferior water dispersibility.

In practice, viscosities of the prepared compositions may be employed as a general rule to determine whether or not they will possess the desired storage stability and dispersibility in water. Compositions having viscosities ranging from about 8,000 to 30,000 cps, as measured with a Brookfield Viscometer, generally will exhibit the desired characteristics.

Water is present in varying amounts depending upon the quantities employed of the other ingredients, always being present in sufficient quantity to serve as the continuous phase for the dispersed pesticide component and to provide, in combination with the other ingredients, 100 parts of finished formulation. In the preferred compositions, i.e., those which incorporate high concentrations of pesticide plus zinc oxide, from about 30 to about 45 parts water will generally be employed per 100 parts of finished formulation.

As described previously herein, minor quantities of one or more components such as antifoaming agents, anticaking agents, freeze-point depressants, protective colloids, preservative and chelants are incorporated into the composition if it is to be stored for any extended period of time prior to use, particularly under adverse storage conditions. Some of these components may also serve as processing aids.

The various, commercially available silicon emulsions are examples of suitable antifoaming agents which may be incorporated in amounts ranging generally from 0.0 to 5.0 parts per 100 parts of the total composition and preferably 0.0 t 1.0 parts per 100. Typical examples of antifoaming agents include silicon emulsions such as, FG-10 and 1510 U.S. from Dow Corning.

To prevent caking of the solid components during dry milling, an anticaking agent may be added to the composition. The anticaking agents prevent the aqueous concentrate from settling into a hard cake and prevent the dry powder from caking. If employed, from 0.0 to 10 and, preferably, 0.5 to 2.0 parts of such materials per each 100 parts of the total composition will generally serve to maintain, in combination with the suspending-dispersing system, the desired storage stability of the composition under the most extreme storage conditions. It is particularly advantageous to incorporate anticaking materials into those compositions of high pesticide content.

Several different types of finely-divided silicas now known in the art are examples of particularly suitable anticaking agents. Suitable anticaking agents include refined kaolin clay, amorphous precipitated silica dioxide, such as Hi Sil 233 available from PPG Industries, or refined clay, such as Hubersil available from Huber Chemical Co., with precipitated silica being preferred. Typically, these agents are present in the composition in 0.0 to 10.0 parts per hundred, and in the preferred embodiment 0.5 to 2.0 parts per hundred.

Lower alkylene glycols, e.g., ethylene or propylene glycol, are examples of suitable freeze-point depressants which are used if the composition is likely to be stored under subtemperate climatic conditions. Amounts of these compounds ranging from about 0 to about 10 parts, per each 100 parts of total composition will adequately provide the composition with the desired antifreeze protection, and in the preferred embodiment, 3.0 to 7.0 parts per 100.

Because the composition will lose viscosity over an extended period of time, preservatives are added to prevent chemical and bacterial degradation of the xanthan gum. The preservative is present in the aqueous composition at a weight of 0.0 to 1.0 parts per one hundred. Preservatives such as formaldehyde and 1,2-benzisothiazolin-3-one may be used with this embodiment of the invention. In the preferred embodiment of the aqueous composition, 1,2-benzoisothiazolin-3-one, available from I.C.I., is employed.

To further ensure that the xanthan gum remains in solution and effective in the aqueous concentrate, a chelating agent may be added to protect the fully hydrated gum from interacting with the zinc and other heavy metals which may be present. It is believed that a strong chelating agent such as those used in the present invention plays a secondary role of aiding the translocation of solubilized zinc into the plant tissue. Commonly used chelating agents such as citrates, hydroxyethylethylenediaminetriacetic acid (HEDTA) and ethylenediaminetetraacetic acid (EDTA) may be used in a volume of 0.0 to 5.0 parts per one hundred. In the preferred embodiment, EDTA is present in a volume of 0.0 to 1.0 parts per hundred.

The aqueous concentrate of this invention may also include a protective colloid. The protective colloid prevents particle to particle agglomeration known as flocculation. Commonly used protective colloids such as starches, polyvinyl alcohols and polyvinyl pyrrolidone may be employed in this invention. Polyvinyl pyrrolidone, available from B.A.S.F., is used in the preferred embodiment. The protective colloid is present in the invention in a volume of 0.0 to 2.0%.

To prepare the concentrate, the order of adding the ingredients is not especially critical, although it is preferred to admix the heteropolysaccharide, surfactant, and any optional components to be incorporated thoroughly in the continuous water phase prior to adding the solid pesticide and zinc oxide components. Preparation of the concentrate may be carried out at ambient temperature with mild agitation, no application of heat or undue pressure normally being needed to obtain the desired homogeneous, flowable suspension. However, further mixing of the concentrate may be carried out employing conventional homogenizing devices, if desired or deemed advisable, to assure the most homogeneous suspension of the pesticide component.

The concentrate of this invention, even if containing a high concentration of pesticide and micronutrient, provides an easily flowable formulation which utilizes water as the sole, inexpensive dispersion medium. This concentrate has excellent bloom characteristics, i.e., it is totally dispersible when added to water. It can be diluted with water in all proportions to provide agglomerate-free, sprayable pesticidal/micronutrient composition of any desired concentration. Preparation of the spray dilution may be easily accomplished at the application site by simply pouring an appropriate amount of the concentrated composition into water within the spray tank or other convenient container. It is also possible to apply the composition in undiluted form, utilizing newer, specialized spray techniques.

The sprayable, agglomerate-free pesticidal-micronutrient compositions formulated from the concentrate of this invention may be applied using conventional spray equipment without causing plugging of the spray nozzles or other malfunction of the spray equipment.

Wettable Powder:

The wettable powder composition of this invention comprises zinc oxide and at least one solid pesticidal ingredient. The nature of its components and the quantities, by weight, of each which constitute the composition of this invention are:

1. 50 to 80% of at least one finely divided essentially water insoluble pesticide;

2. 3.0–15.0% of zinc oxide;
3. 2.0–6.0% of a dispersing agent;
4. 0.5–2.0% of a wetting agent;
5. 0.6–40.0% of a diluent;
6. 0.1–2.0% of a grinding agent; and
7. 0.0–2.0% of a solid chelating agent.

The pesticidal agents and zinc oxide properties have already been discussed. In general, the pesticide content of the wettable powder compositions of this invention may vary from about 50 to 80%, by weight. In those compositions, the preferred content ranges from 70–80% by weight. This composition also employs a pesticidal component and zinc oxide having an average particle size of 1 to 10 microns and, in the preferred embodiment, an average particle size of less than 3.5 microns.

The dispersing agents used with the wettable powder can be anionic ligands with sodium lignosulfonate and sodium naphthalene sulfonate formaldehyde condensate being preferred. The dispersing agent stabilizes the final spray dilution from flocculation and agglomeration. The wettable powder composition includes the dispersing agent in a concentration of 2.0 to 6.0 parts per hundred in one embodiment and 4.0 to 6.0 parts per hundred in the preferred embodiment.

The wetting agents used in the wettable powder act to make the composition more susceptible to wetting out and to forming a suspension in an aqueous medium by reducing the surface tension of the water. The wetting agents used with this formulation include dioctyl-sodium sulfosuccinate, ethylene oxide propylene oxide block copolymer, alkyl-napthanene sulfonates, and alkylaryl polyether alcohols of the general formula described above. The wetting agent is present in 0.5 to 3.0 parts per hundred and, in the preferred embodiment, 0.5 to 1.5 parts per hundred.

The diluents used in the powder formulation of the invention include kaolin clay, amorphous silica, and smectite clays. The diluent acts to dilute the active components to their desired levels. The diluent is present in the invention in a range of 0.6 to 40.0 parts per hundred and, in the preferred embodiment, in an amount of about 5.0 to 10.0 parts per hundred.

Conventional grinding aids such as refined clays and amorphous silica may be used in the powder composition. The preferred grinding aid is amorphous silica. This invention may contain 0.1 to 2.0 parts per hundred of the grinding aid, with the preferred amount being 0.3 to 1.5 parts per hundred.

A dry chelating agent may be added to enhance the uptake of the zinc nutrient by the plant foliage. This invention may contain 0.0 to 2.0 parts per 100 of chelants such as the sodium salt of EDTA.

Dispersible Spray Dried Granule:

The spray dried dispersible granule formulation of this invention includes at least one water insoluble pesticidal composition plus the micronutrient. The nature of the components and the quantities of each which constitute the spray dried granule composition of this invention are, by weight, the following:

1. 50–75% of at least one finely-divided essentially water insoluble pesticide;
2. 7.0–15.0% of zinc oxide, finely divided;
3. 2.0–20% of a dispersing agent;
4. 0.0–10.0% of a wetting agent;
5. 0.0–2.0% of an antifoaming agent;
6. 0.0–10.0% of a diluent; and
7. 0.0–2.0% of a chelant.

The pesticide, zinc oxide, dispersing agents, wetting agents, chelating agent and diluents used with this embodiment of the invention are described above. The pesticide and zinc oxide will have the same particle sizes as described in the discussion of the wettable powder. The dispersing agent is present in 2.0 to 20 parts per hundred and, preferably, 10 to 12 parts per hundred. The wetting agent has a volume of 0.0 to 10 parts per hundred with 1.0 to 4.0 parts per hundred being preferred. The chelant can be used in the same amounts it is used in the wettable powder. Finally, the diluent is present in a volume of 0.0 to 10.0% parts per hundred with 0.0 to 5.0 parts per hundred being preferred.

The spray dried dispersible granule may also include an antifoaming agent to prevent foaming during processing and spray applications. These antifoaming agents may be any of the commercially available antifoaming agents such as the silicon emulsions described above. The antifoaming agent has a volume of 0.0 to 1.0 parts per hundred and a volume of 0.0 to 0.5 parts per hundred in the preferred embodiment.

For a fuller understanding of the nature of the invention and the methods for carrying it out, the following illustrative examples are given. In these examples and elsewhere herein, where quantities of ingredients may be given in parts, such proportions are by weight, unless otherwise indicated.

EXAMPLES

Example 1

An aqueous concentrate is prepared from the following formulation:

| Component | % by Weight |
| --- | --- |
| Chlorothalonil | 40.0 |
| Zinc Oxide | 5.6 |
| Pluronic P-104 (poly (oxypropylene) block polymer with poly (oxyethylene) available from B.A.S.F.) | 6.0 |
| Xanthan Gum (available from Kelco) | 0.25 |
| Antifoam FG-10 (Silicon emulsion, available from Dow Corning) | 0.25 |
| Hi Sil 233 (Precipitated amorphous silica available from PPG Ind.) | 1.0 |
| PVP K-30 (Polyvinylpyrrolidone available B.A.S.F.) | 0.4 |
| Propylene Glycol | 3.0 |
| Proxel GXL (1,2-Benzisothiazolin-3-one available from I.C.I.) | 0.1 |
| EDTA | 1.5 |
| Water | 41.9 |

The ingredients are mixed together under high sheer agitation. The mixture is then passed through a wet milling system such as a stirred ball mill or high speed media mill. The milling is continued until a final average particle size of approximately 3 microns is achieved.

The water and surfactants are generally added first followed by the pesticide and zinc oxide. The xanthan gum may be added with the surfactants or after the milling has been completed.

Example 2

A wettable powder formulation of the composition may also be created. The powder has the following formulation:

| Component | % by Weight |
| --- | --- |
| Chlorothalonil | 75.0 |
| Zinc Oxide | 10.4 |
| Polyfon T (Sodium Lignosulfonate available from Westvaco) | 5.0 |
| Aersol OTB (Dioctyl sodium sulfosuccinate available from American Cyanamid) | 1.0 |
| Bardin Clay (Kaolin clay available from Huber) | 8.1 |
| Hi Sil 233 | 0.5 |

Initially the above ingredients are blended together. The blend is then hammer milled forming a coarsely milled mixture. The mixture is then reblended and air milled to an average particle size of approximately 3.5 microns.

Example 3

A spray dried dispersible granule may also be produced. This granule has the following ingredients:

| Component | % by Weight |
| --- | --- |
| Chlorothalonil | 75.0 |
| Zinc Oxide | 10.4 |
| Polyfon T | 10.9 |
| Petro BP (Alkylnapthalene sodium sulfonate available from Witco) | 3.0 |
| Antifoam FG-10 | 0.2 |
| Bardin Clay | 0.25 |

First the ingredients are mixed together in no particular order. Second, the mixture is passed through a wet milling system, either a stirred ball mill or high speed small media mill. Third, the milling is continued until a final average particle size of approximately three microns results. The resulting slurry is then spray dried at 90° C. (inlet temperature) to a final moisture level of about 2%. An alternate method would be to blend/hammer mill and air mill the ingredients together followed by dispersion into water under moderate agitation and then spray drying.

Having described the invention in detail and by reference to preferred embodiments thereof, it will be apparent that modifications and variations are possible without departing from the scope of the invention defined in the appended claims.

What is claimed is:

1. An aqueous pesticidal-micronutrient composition which is readily dilutable in water to provide an effective amount of pesticide-zinc nutrient for spray application to crops which, prior to dilution, comprises, by weight of the total composition:

(a) about 10 to 60% chlorothalonil having an average particle size of approximately 1 to 10 microns;
   (b) about 1.0 to 10% of at least one nonionic surfactant;
   (c) about 0.02 to 1.0% of a heteropolysaccharide gum;
   (d) about 1.0 to 10% zinc oxide having an average particle size of 1 to 10 microns; and
   the balance being water.

2. The aqueous pesticidal-micronutrient composition of claim 1 further including:

(e) up to about 8.0% anionic surfactant;
   (f) up to about 5.0% antifoam agent;
   (g) up to about 10.0% anticaking agent;
   (h) up to about 2.0% protective colloid;
   (i) up to about 10.0% freeze point depressant;
   (j) up to about 1.0% preservative; and
   (k) up to about 5.0% chelating agent.

3. The aqueous pesticidal-micronutrient composition of claim 2 wherein said concentrate comprises:

(a) about 35 to 55% chlorothalonil having an average particle size of 2.0 to 4.0 microns;
   (b) about 3.0 to 7.0% of the nonionic surfactant;
   (c) about 0.05 to 0.75% of the heteropolysaccharide gum;
   (d) about 2.0 to 7.0% zinc oxide having an average particle size of 1.0 to 4.0 microns;
   (e) about 0.0 to 8.0% of the anionic surfactant;
   (f) about 0.0 to 1.0% of the antifoam agent;
   (g) about 0.5 to 2.0% of the anticaking agent;
   (h) about 0.0 to 2.0% of the protective colloid;
   (i) about 2.0 to 7.0% of the freeze point depressant;
   (j) about 0.0 to 1.0% of the preservative; and
   (k) about 0.0 to 1.0% of the chelating agent.

4. The aqueous pesticidal-micronutrient composition of claim 3 wherein the nonionic surfactant is selected from the group consisting of an alkylaryl polyether alcohol, tristyrlphenol and a block copolymer of ethylene oxide and propylene oxide; the heteropolysaccharide gum is xanthan gum; the antifoam agent is a silicon emulsion; the anticaking agent is amorphous silica; the protective colloid is polyvinyl pyrrolidone; the freeze point depressant is selected from the group consisting of ethylene glycol and propylene glycol; the preservative is 1,2-benzisothiazolin-3-one; and the chelating agent is ethylenediaminetetraacetic acid.

5. A pesticidal-zinc micronutrient composition in the form of a wettable powder which comprises, by weight:

(a) about 50 to 80% chlorothalonil having a 2.0 to 4.0 microns average particle size;
   (b) about 7.0 to 15.0% zinc oxide of an average particle size of 1.0 to 4.0 microns;
   (c) about 1.0 to 6.0% of a dispersing agent;
   (d) about 0.5 to 2.0% of a wetting agent;
   (e) about 0.6 to 40.0% of a diluent;
   (f) about 0.1 to 1.0% of a grinding aid; and
   (g) about 0.1 to 5.0% of a chelating agent.

6. The pesticidal-zinc micronutrient wettable powder composition of claim 5, which comprises:

(a) about 70 to 80% chlorothalonil;
   (b) about 9.0 to 12.0% zinc oxide;
   (c) about 2.0 to 6.0% of the dispersing agent;
   (d) about 0.5 to 1.5% of the wetting agent;
   (e) about 5.0 to 10% of the diluent;
   (f) about 0.3 to 0.8% of the grinding aid; and
   (g) about 0.2 to 2.0% of the chelating agent.

7. The pesticidal-zinc micronutrient wettable powder composition of claim 6 wherein the dispersing agent is selected from the group consisting of sodium lignosulfonates and sodium naphthalenesulfonate formaldehyde condensates; the wetting agent is selected from the group consisting of dioctyl sodium sulfosuccinate, alkylaryl polyether alcohols, sodium alkylnaphthylene sulfonates and block copolymers of ethylene oxide and propylene oxide; the diluent is selected from the group consisting of bardin clay and amorphous silica; the grinding aid is amorphous silica; and the chelating agent is selected from the group consisting of hydroxyethylethylenediaminetriacetic acid and ethylenediaminetetraacetic acid.

8. A pesticidal-zinc wettable powder composition in the form of a spray dried dispersible granule, comprising, by weight percent of total composition:
   (a) about 50 to 80% chlorothalonil having a 2 to 4 micron average particle size;
   (b) about 6.5 to 15% zinc oxide having a 1 to 4 micron average particle size; and
   (c) about 2.0 to 20% of a dispersing agent.

9. The pesticidal-zinc granule composition of claim 8 further including, by weight percent of total concentrate:
   (d) about 0.0 to 10.0% wetting agent;
   (e) about 0.0 to 1.0% antifoaming agent;
   (f) about 0.0 to 10.0% diluent; and
   (g) about 0.0 to 5.0% chelating agent.

10. The pesticidal-zinc composition of claim 9, which by weight percent of total concentrate comprises:
   (a) about 70 to 80% chlorothalonil;
   (b) about 8 to 12% of zinc oxide;
   (c) about 6 to 12% of the dispersing agent;
   (d) about 1.0 to 4.0% of the wetting agent;
   (e) about 0.0 to 0.5% of the antifoaming agent;
   (f) about 0.0 to 1.0% of the diluent; and
   (g) about 0.1 to 2.0% of the chelating agent.

11. The pesticidal-zinc granule composition of claim 10 wherein the dispersing agent is selected from the group consisting of sodium lignosulfonates and sodium naphthalenesulfonate formaldehyde condensates; the wetting agent is selected from the group consisting of dioctyl sodium sulfosuccinate, block copolymers of ethylene oxide and propylene oxide, sodium alkylnaphthylene sulfonates and alkylaryl polyether alcohols; the antifoaming agent is silicon emulsion; the diluent is selected from the group consisting of kaolin clay and amorphous silica; and the chelating agent is selected from the group consisting of ethylenediaminetetraacetic acid and hydroxyethylethylenediaminetriacetic acid.

12. A pesticidal composition for application to plant foliage which consists essentially of chlorothalonil and zinc oxide, said chlorothalonil being present in the composition in an amount that is pesticidally effective when the composition is formulated into an aqueous spray and applied to the plant foliage and said zinc oxide being present in an amount which is effective as a micronutrient when the composition is formulated into an aqueous spray and applied to the plant foliage with said chlorothalonil.

13. The pesticidal composition of claim 12 wherein the composition is an aqueous concentrate, a wettable powder or a dispersible granule which can be mixed with water to form an aqueous spray.

14. The pesticidal composition of claim 12 wherein the composition is formulated for application to potatoes.

15. The pesticidal composition of claim 12 wherein the composition is formulated as an aqueous concentrate and ethylene diamine tetraacetic acid and polyvinyl pyrrolidone are present in said composition.

16. The pesticidal composition of claim 12 wherein the composition is an aqueous spray formulated from an aqueous concentrate, a wettable powder or a dispersible granule.

17. The pesticidal composition of claim 12 wherein the composition is an aqueous composition and a nonionic surfactant is present in said composition with said chlorothalonil and said zinc oxide.

18. The pesticidal composition of claim 12 wherein the zinc oxide has an average particle size less than 3.5 microns.

19. An aqueous spray composition for application to plant foliage which consists essentially of chlorothalonil and zinc oxide, said aqueous spray being formulated from an aqueous concentrate, a wettable powder, or a dispersible granule which consists essentially of chlorothalonil and zinc oxide, said chlorothalonil being present in the composition in an amount that is pesticidally effective when the composition is applied to the plant foliage and said zinc oxide having a particle size less than 10 microns and being present in an amount which is effective as a micronutrient when the composition is applied to the plant foliage with said chlorothalonil.

* * * * *